United States Patent [19]
Nordan

[11] Patent Number: 4,662,881
[45] Date of Patent: May 5, 1987

[54] EPIKERATOPHAKIA PROCESS

[76] Inventor: Lee T. Nordan, 4718 Vista de la Tierra, Del Mar, Calif. 92014

[21] Appl. No.: 820,066

[22] Filed: Jan. 21, 1986

[51] Int. Cl.⁴ .................. A61F 2/14; A61F 17/32; A61B 19/00
[52] U.S. Cl. ................................ 623/5; 128/1 R; 128/305
[58] Field of Search .............. 623/4, 5, 6; 128/1 R, 128/305, 305.1

[56] References Cited

U.S. PATENT DOCUMENTS

| | | |
|---|---|---|
| 4,346,482 | 8/1982 | Tennant et al. ............... 128/1 R X |
| 4,565,198 | 1/1986 | Koeniger ............................ 128/305 |
| 4,607,617 | 8/1986 | Choyce ............................ 623/5 X |

FOREIGN PATENT DOCUMENTS 993937 2/1983 U.S.S.R. ............................ 623/5

OTHER PUBLICATIONS

"Corneal Surgery", (Book) by Louis J. Girard, vol. two, published by C. V. Mosby Co., St. Louis, Torono, London, 1981, p. 171 and FIGS. 6-26 relied upon.

Primary Examiner—Ronald L. Frinks
Attorney, Agent, or Firm—Charmasson & Holz

[57] ABSTRACT

A process for practicing refractive surgery on a patient's eye by grafting a donor cornea shaped into a lenticle to the front of the patient's cornea. The periphery of the donor cornea is chamfered to a bevelled edge and a corresponding slanted peripheral corneal groove is cut into the patient's cornea. The bevelled edges of the lenticle is then inserted into the groove and then sutured to the patient's cornea.

10 Claims, 7 Drawing Figures

EPIKERATOPHAKIA PROCESS

BACKGROUND OF THE INVENTION

The invention relates to corrective eye surgery and in particular to refractive surgery using part of a donor cornea grafted in front of the patient's cornea known as epikeratophakia.

Epikeratophakia is a relatively new concept in refractive surgery developed by Dr. Herbert Kaufman. It has been dubbed "the living contact lens", and has been offered as a simple and safer process than keratomileusis technique developed by the Instituto Barraquer of Bogota, Colombia. Instead of reshaping the anterior portion of the patient's own cornea as in the keratomileusis process, epikeratophakia uses a slice of donor cornea shaped into a lenticle and then sutured to the front of the patient's own cornea.

FIGS. 1 and 2 diagrammatically illustrate the prior art in the practice of epikeratophakia. FIG. 1 shows a slice 1 of a donor's cornea 2 being shaved off by means of a micro-keratome knife 3. The knife 3 has a sole 4 which, when applied to the cornea 2, flattens its top. An oscillating blade 5 passing through a slot 6 in the sole 4 cuts a slice 1 of the cornea which in its natural unrestrained shape appears as shown in FIG. 2. The posterior or concave face of the slice or lenticle 1, is then ground to obtain the proper refractive correction required by the patient by removing the shaded area 7. On the patient's cornea 8 a peripheral groove 9 is cut to receive the base 10 of the corrected lenticle 1, which is then sutured to the patient's cornea 8. The shape and width of the peripheral groove 9 is normally achieved by two slicing operations. The first is directed perpendicularly to the axis of vision to form the base 11 of the groove. The second is directed parallelly to the axis of vision to form the inner wall of the groove 12. The matching of the base 10 of the lenticle 1 with the peripheral groove 9 is often difficult to control. The cutting of the groove itself by means of two types of trephines is a difficult operation which requires great skill and precision.

SUMMARY OF THE INVENTION

The invention offers an improved process for preparing the donor lenticle and installing it on the patient's cornea in an epikeratophakia operation. The principal object of the invention is to simplify the cutting of the peripheral groove on the recipient's cornea. Another object of the invention is to facilitate the placement of the donor lenticle on the patient's cornea. A further object is to provide for an easier suturing of the lenticle. This and other valuable objects are accomplished by chamfering the periphery of the lenticle to a bevelled narrow edge and by cutting a slanted peripheral groove into the patient's cornea which is commensurate with the bevelled edge. The result is a more stable positioning of the lenticle which facilitates the suturing process. The peripheral groove can be cut in a single operation and cause minimal disturbance on the face of the patient's cornea.

DESCRIPTION OF THE PREFERRED EMBODIMENT OF THE INVENTION

Figure 1:
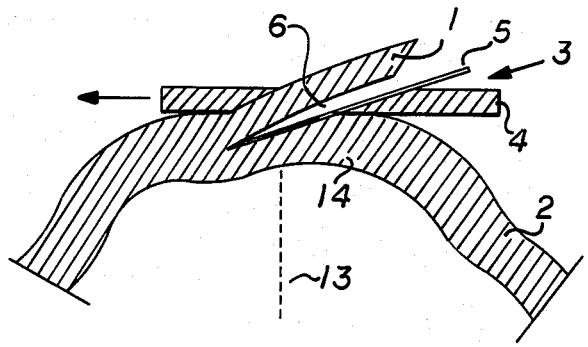
FIG. 1 illustrates diagrammatically the slicing of a live lenticle from a donor's cornea by means of a micro-keratome knife.

In the practice of the improved epikeratophakia process, the prosthetic lens or lenticle 1 is taken from a donor as illustrated in FIG. 1 by means of a micro-keratome or any other slicing device. It should be noted that the lenticle is sliced in a direction perpendicular to the axis of vision 13, and that the entire prosthesis is taken from the substantia propria 14, without cutting through the cornea 2.

Figure 3:
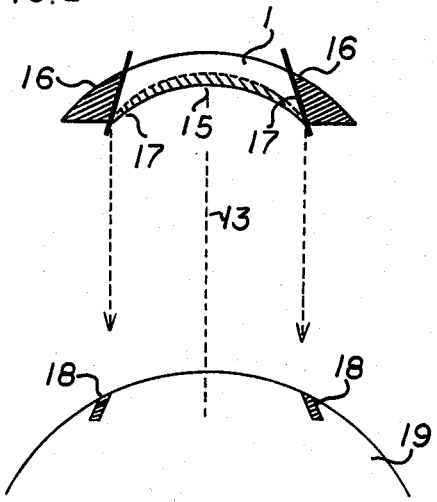
FIG. 3 is a diagrammatical illustration of the improved process of epikeratophakia.

The hyperopic or myopic correction required by the patient is then applied by carving the posterior face of the lenticle and removing the shaded portion 15 illustrated in FIG. 3. The carving is oest accomplished by freezing the lenticle on a cryogenic lathe or other equivalent device. The periphery of the lenticle 1 is then chamfered to form bevelled edge 16 which is intercepting the edge 17 of the dome formed on the posterior face of the lenticle. The edge 16 forms an angle of between 15 and 25 degrees with the axis of vision 13, and is slanted outwardly toward said axis.

Figure 4:
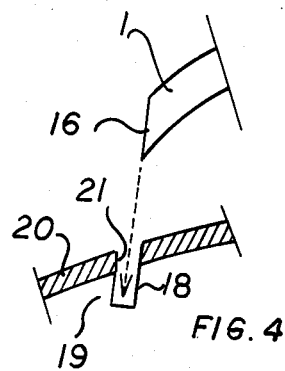
FIG. 4 is a detailed illustration of the match between the bevelled edge of a lenticle and the recipient's groove.
Figure 2:
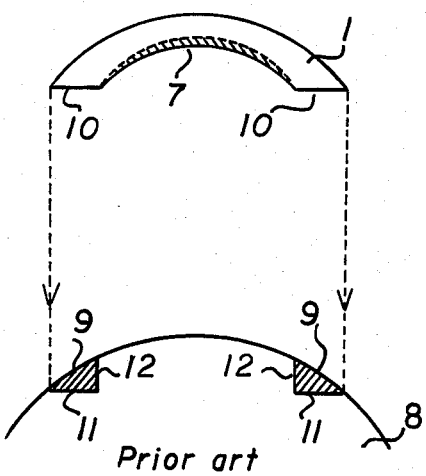
FIG. 2 is a diagrammatical illustration of the prior art process of epikeratophakia.

A peripheral corneal groove 18 is cut on the patient's cornea 19 with a slant congruent with the chamfered edge 16 of the lenticle. As shown in FIG. 4, the groove extends through the Bowman's membrane 20 and into the cornea to a depth of between 0.2 and 0.4 millimeters.

Figure 5:
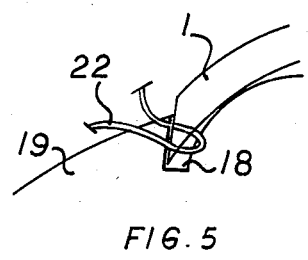
FIG. 5 illustrates the suturing of the lenticle to the patient's cornea.

Since the edge of the lenticle and the outer wall 21 of the groove 18 are congruent, the lenticle must be slightly compressed in order to insert it into the groove. Once inserted, the lenticle assumes a very stable position which greatly facilitates the suturing process illustrated in FIG. 5. Micro-suture 22 can conveniently be run back and forth through the edge of the lenticle and the peripheral area of the cornea around the groove 18.

Figure 6:
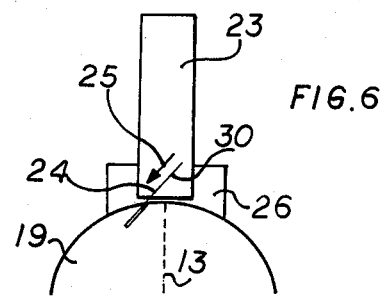
FIG. 6 illustrates diagrammatically the cutting of a slated peripheral groove by means of a trephine with slanted and translated blade.

FIG. 6 illustrates the process of cutting the peripheral groove 18 by means of a trephine 23 having a slanted blade 24. A translating movement, about a conical plane having its apex 30 on the patient's axis of vision 13, indicated by the arrow 25 is imparted to the blade 24 as it is rotated inside the stabilizing base 26.

Figure 7:
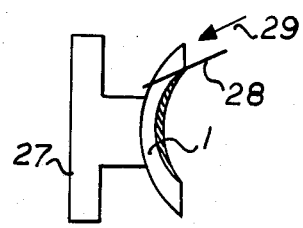
FIG. 7 illustrates the chamfering of the edge of the lenticle.

FIG. 7 illustrates the chamfering of the lenticle 1 while it is mounted on the anvil 27 of a cryogenic lathe. The chamfering tool 28 is rotated about the axis of the lathe, which also corresponds to the axis of vision, and advanced progressively as indicated by the arrow 29 until desired peripheral edge on the lenticle is obtained. It should be understood that other means for cutting the peripheral groove and for chamfering the edge of the lenticle 1 could be used other than those described herein.

It should be noted that a variety of prosthetic lenticles with different refractive indicia can be prepared in advance, all having the same dimensions and chamfering characteristics, to be stored then selected and installed as required by a plurality of patients.

While the preferred embodiment of the invention has been described and alternate processes have been suggested, other embodiments and modifications could be devised without departing form the spirit of the invention and the scope of the appended claims.

What is claimed is:

1. A process for practicing an epikeratophakia operation on a patient's cornea which comprise the steps of:
    forming a prosthetic lenticle by removing the anterior section of cornea from a donor's organ by slicing through the substantia propria cornea in a plane perpendicular to the axis of vision;
    shaping the prosthetic lenticle by carving its posterior face into a dome having a radius corresponding to the hyperopic or myopic correction required by the patient;
    chamfering the periphery of the prosthetic lenticle to create a peripheral wall intercepting the edge of said dome and slanting outwardly toward said axis of vision;
    cutting a shallow slanted peripheral groove in the patient's cornea, the outer wall of said groove being congruent with the chamfered wall of the prosthetic lenticle;
    inserting the edge of the prosthetic lenticle into said peripheral groove; and
    suturing said edge to the patient's cornea.

2. The process of claim 1 wherein said step of cutting a peripheral groove comprise rotating a cutting blade along a conical plane having it apex on the patient's axis of vision anteriorly to the surface of said patient's cornea, and advancing said blade into said cornea along said conical plane.

3. The process of claim 2, wherein said blade is advanced into said cornea to a depth of 0.2 to 0.4 millimeters.

4. The process of claim 1, wherein the steps of shaping and chamfering the prosthetic lenticle comprise freezing the lenticle.

5. The process of claim 4, wherein said shaping and chamfering is done on a cryogenic lathe.

6. The process of claim 5, wherein the edge of the prosthetic lenticle forms an angle with said axis of vision of between 15 and 25 degrees.

7. A prosthetic lenticle for installation in front of a patient's cornea which is removed from the anterior portion of a donor's cornea and whose posterior face is carved to form a concave surface corresponding to the patient's required refractive correction, wherein said lenticle has its periphery chamfered to form a slanted edge intercepting said concave surface and defining a conical plane having its apex on the axis of vision of the lenticle ahead of its anterior surface.

8. The prosthetic lenticle claimed in claim 7, wherein said conical surface forms an angle between 15 and 25 degrees with said axis.

9. A process for practicing an epikeratophakia operation on a patient's cornea which comprises the steps of:
    forming a prosthetic lenticle having the shape of a spherical segment generally commensurate with the patient's cornea;
    shaping the prosthetic lenticle by carving its posterior face into a dome having a radius corresponding to the hyperopic or myopic correction required by the patient;
    chamfering the periphery of the prosthetic lenticle to create a peripheral wall intercepting the edge of said dome and slanting outwardly toward the axis of vision of said lenticle;
    cutting a shallow slanted peripheral groove in the patient's cornea, the outer wall of said groove being congruent with the chamfered wall of the prosthetic lenticle;
    inserting the edge of the prosthetic lenticle into said peripheral groove; and
    suturing said edge to the patient's cornea.

10. The process of claim 9, wherein said step of cutting a peripheral groove comprise rotating a cutting blade along a conical plane having it apex on the patient's axis of vision anteriorly to the surface of said patient's cornea, and advancing said blade into said cornea along said conical plane.

* * * * *